US006814985B1

(12) United States Patent
Hu

(10) Patent No.: US 6,814,985 B1
(45) Date of Patent: Nov. 9, 2004

(54) HERBAL COMPOSITIONS AND USES FOR THE TREATMENT OF ALLERGIC REACTIONS

(75) Inventor: Guorang Hu, Fairfield (AU)

(73) Assignee: G & W Aust Pty. Ltd., Fairfield (AU)

( * ) Notice: Subject to any disclaimer, the term of this patent is extended or adjusted under 35 U.S.C. 154(b) by 0 days.

(21) Appl. No.: 09/937,721

(22) PCT Filed: Mar. 31, 2000

(86) PCT No.: PCT/AU00/00270

§ 371 (c)(1),
(2), (4) Date: Sep. 28, 2001

(87) PCT Pub. No.: WO00/59520

PCT Pub. Date: Oct. 12, 2000

(30) Foreign Application Priority Data

Apr. 1, 1999 (AU) .............................................. PP9587
Jun. 23, 1999 (AU) .............................................. PQ1147

(51) Int. Cl.[7] .............................................. A61K 35/78
(52) U.S. Cl. ........................ 424/725; 424/735; 424/739; 424/741; 424/747; 424/752
(58) Field of Search ................................ 424/725, 735, 424/739, 741, 747, 752

(56) References Cited

U.S. PATENT DOCUMENTS 5,466,452 A * 11/1995 Whittle ........................ 424/750

FOREIGN PATENT DOCUMENTS

| CN | 1149481 | * | 5/1997 |
| JP | 06256203 | * | 9/1994 |
| JP | 06279305 | * | 10/1994 |

OTHER PUBLICATIONS

Reid, A Handbook of Chinese Healing Herbs, Barnes and Noble, Inc., New York, 1995, pp. 202–207.*
Fontanarosa PB, Lundberg GD. Alternative medicine meets science. JAMA. Nov. 11, 1998; 280(18):1618–9.
Hu G, Walls RS, Bass D, Ramon B, Grayson D, Jones M, Gebski V. The Chinese herbal formulation biminne in management of perennial allergic rhinitis: a randomized, double– blind, placebo–controlled, 12–week clinical trial. Ann Allergy Asthma Immunol. May 2002; 88(5):478–87.
Margolin A, Avants SK, Kleber HD. Investigating alternative medicine therapies in randomized controlled trials. JAMA. Nov. 11, 1998; 280(18):1626–8.
Marwick C. Alterations are ahead at the OAM (Office of Alternative Medicine). JAMA. Nov. 11, 1998; 280(18):1553–4.
Shen Z, Hu G, Shi S, Zhang L, Wu B, Chen W, Chen S, Tu H, Huang J. The preventative value and curative mechanism of 'Wen Yang Pill' against seasonal attack of bronchial asthma. Fourth International Congress of Oriental Medicine, Kyoto, Japan, 1985.
Ziyin, S. et al., *Journal of Traditional Chinese Medicine,* 2(2): 135–140 (1982).
Rudolf Fritz Weiss, M.D., "Herbal Medicine," translated from the Sixth German Edition of *Lehrbuch der Phytotherapie* by A.R. Meuss, FIL, MITI; AB Arcanum, Gothenburg, Sweden; Beaconsfield Publishers Ltd., Beaconsfield, England (pp. 218–222).

* cited by examiner

Primary Examiner—Jean C. Witz

(57) ABSTRACT

The present invention relates generally to a composition for the treatment or prophylaxis of allergic and inflammatory reactions such as but not limited to Type I hypersensitivity reactions in mammals. More particularly, the present invention is directed to compositions comprising herbs or extracts of herbs or botanical or horticultural equivalents of the herbs or chemical or functional equivalents of the herbal extracts useful in the treatment or prophylaxis of allergic and inflammatory reactions such as but not limited to respiratory disorders. The present invention further contemplates a method of treating allergic and inflammatory reactions in mammals and in particular Type I hypersensitivity disorders and even more particularly respiratory disorders by the administration of a herbal composition or its chemical or functional equivalent.

5 Claims, 14 Drawing Sheets

HERBAL COMPOSITIONS AND USES FOR THE TREATMENT OF ALLERGIC REACTIONS

FIELD OF THE INVENTION

The present invention relates generally to a composition for the treatment or prophylaxis of allergic and inflammatory reactions such as but not limited to Type I hypersensitivity reactions in mammals. More particularly, the present invention is directed to compositions comprising herbs or extracts of herbs or botanical or horticultural equivalents of the herbs or chemical or functional equivalents of the herbal extracts useful in the treatment or prophylaxis of allergic and inflammatory reactions such as but not limited to respiratory disorders. The present invention further contemplates a method of treating allergic and inflammatory reactions in mammals and in particular Type I hypersensitivity disorders and even more particularly respiratory disorders by the administration of a herbal composition or its chemical or functional equivalent.

BACKGROUND OF THE INVENTION

Allergic and inflammatory reactions in mammals are responsible for conditions which range from minor discomfort to death. The latter is particularly the case following, for example, a compromised respiratory system resulting from an allergic reaction in the nasal or bronchial passages.

An example of a less severe allergic reaction in the respiratory system is allergic rhinitis. Allergic rhinitis generally occurs when a sensitized individual is re-exposed to a foreign substance or allergen. The first exposure by the individual generates allergen-specific antibodies and, in particular, IgE antibodies. This process is generally facilitated by the production of IL-4 by helper T cells. The IgE antibodies bind to mast cells via the Fcε R1 receptor. Once sufficient IgE antibodies are present on the surface of mast cells, exposure to the same allergen induces mast-cell activation and acute allergic reaction. The specific result is allergic rhinitis or hayfever. The most common form of hayfever results from exposure to pollen. The allergic reaction is not so much from pollen per se but from allergenic proteins present in the pollen. Mast cells carrying surface allergen-specific IgE molecules release inflammatory mediators once the IgE antibodies are cross-linked by the allergens. The inflammatory mediators are contained in secretary granules. Antigen cross-linking of bound IgE antibodies triggers rapid local inflammation and eventually the symptoms of hayfever and asthma.

One of the inflammatory mediators is histamine. Although there is no known cure for allergic rhinitis, symptomatic-based therapies have been developed which include the administration of anti-histamines to reduce the inflammatory effects of histamines.

Herbal formulations comprising extracts of more than one herbal plant have been used for centuries in Traditional Chinese Medicine (TCM). There is now an increasing acceptance of their value and therapeutic efficacy in Western medicine. TCM has its own unique and philosophical theory in etiology pathology, diagnosis, pharmacology and therapeutics. Many concepts surrounding TCM have particular relevance to Western medicine such as viewing parts of the body as an organic whole, considering inter-relations and influences between organs and being aware of relevant adaptation of the human body to the natural environment.

There are two major principles in the utilization of herbs in the management of diseases: individualized treatment and the use of herbal formulations.

Herbal formulations have been previously described in the literature in the treatment of respiratory disorders. For example, Shen Ziyin and colleagues, *Journal of Traditional Chinese Medicine* 2: 135–140, 1998 describe the use of a mixture of herbs including *Radix Aconiti, Radix Rehmanniae Praeparata,* Rhizoma, Dioscoreae, *Fructus Corni, Herba Eistanchis, Herba Epimedii, Fructus Psoraleae, Semen Cuscutae* and *Pericarpium Citri Reticulatae.* These herbs were selected to restore Kidney-yang in a treatment known as Kidney Reinforcement Regimen (KRR). It was proposed that the KRR induced by the administration of the above mixture of herbs strengthened the function of the hypotbalamus-pituitary-adrenocortical axis and this modulated immunological function in the treatment of seasonal asthma.

Another herbal formulation is referred to as the "Wen Yang Pill" and was described by Shen Ziyin and colleagues at the 4th International Congress of Oriental Medicine, Kyoto, Japan in 1985. The Wen Yang Pill comprises the herbs *Radix Aconiti, Radix Rehmanniae, Radix Dioscoreae oppositae, Herba Epimedii, Semen Psoraeleae* and *Semen cuscuatae.*

However, despite a large range of herbal formulations being described, very few have been the subject of properly controlled studies especially in relation to the treatment of respiratory disorders.

In work leading up to the present invention, the inventor identified a herbal formulation which was shown in randomized, double-blind, placebo-controlled, parallel-grouped clinical trials to be effective in the treatment of allergic and inflammatory reactions in mammals. The herbal formulation of the present invention is particularly useful in the treatment or prophylaxis of Type I hypersensitivity reactions such as but not limited to IgE-based respiratory disorders.

SUMMARY OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

One aspect of the present invention provides a composition comprising herbs or an extract of herbs or botanical or horticultural equivalents of herbs or chemical or functional equivalents of the herbal extract wherein said composition is effective in the prophylaxis or treatment of an allergic or inflammatory response.

Another aspect of the present invention is directed to a composition comprising herbs or an extract of herbs or botanical or horticultural equivalents of herbs or chemical or functional equivalents of the herbal extract wherein said composition is effective in the prophylaxis or treatment of an allergic or inflammatory response as determined by a placebo-controlled trial.

A further aspect of the present invention comprises a composition comprising herbs or an extract of herbs or botanical or horticultural equivalents of herbs of chemical or functional equivalents of the herbal extract wherein said composition is effective in the prophylaxis or treatment of an allergic or inflammatory response and wherein said herbs in the composition are selected to:

(i) keep airways open;
(ii) invigorate the spleen and digestive system;
(iii) reinforce the kidney and function of the urinary and reproductive tract;
(iv) eliminate inflammation; and
(v) promote blood circulation and remove blood stasis.

Yet another aspect of the present invention is directed to a composition comprising herbs or an extract of herbs of botanical or horticultural equivalents of herbs or chemical of functional equivalents of the herb extract wherein said composition is effective in the prophylaxis or treatment of an allergic or inflammatory response and wherein said herbs in the composition are selected from first, second, third, fourth and fifth groups of herbs wherein the first groups comprises: Mahuang, Guizhi, Cangerzi, Xinyi, Bohe, Xixin, xingren, Chaihu, Yinxingye, Baizi and Fangfeng; the second group comprises: Baizhu, Shanyao, Dangshen, Dazao, Gancao, Huangqi and Huangjing; the third group comprises: Tusizi, Roucongrong, Fuzi, Yinyanghuo, Buguzhi, Dihuang and Xianmao; the fourth group comprises: Huangqin, Wumei and Wuweizi; the fifth group comprises: Taoren, Chuanxiong, Danpi and Chishao.

Still another aspect of the present invention contemplates a composition comprising five or more herbs or extracts thereof or botanical or horticultural equivalents of the herbs or chemical or functional equivalents of the herbal extracts, said herbs selected from the list comprising at least one from five groups of herbs wherein the first group comprises: Mahuang, Guizhi, Cangerzi, Xinyi, Bohe, Xixin, Xingren, Chaihu, Yinxingye, Baizi and Fangfeng; the second group comprises: Baizhu, Shanyao, Dangshen, Dazao, Gancao, Huangqi and Huangjing; the third group comprises: Tusizi, Roucongrong, Fuzi, Yinyanghuo, Buguzhi, Dihuang and Xianmao; the fourth group comprises: Huangqin, Wumei and Wuweizi; the fifth group comprises: Taoren, Chuanxiong, Danpi and Chishao.

Even still another aspect of the present invention provides a composition comprises five or more herbs or extracts of five or more herbs selected from the list comprising:

the rhizome of *Rehmannia Glutinosa Libosch,* Dihuang; the root of *Scutellaria Baicalenis Georgi,* Huangqin; the rhizome of *Polygonatum Sibiricum Redout,* Huangjing; the leaf of *Ginkgo Bilobo,* Yinxingye; the leaf of *Epimedium Sagittatum,* Yinyanghuo; the ripe fruit of *Psoralea Corylifolia,* Buguzhi; the fruit of *Schisandra Chinensis Baill,* Wuweizi; the unripe fruit of *Prunus Mume Sieb* without seed, Wumei; the root of *Ledebouriella Divaricata Hiroe,* Fangfeng; the root of *Angelcae Dahuricae,* Baizi; the root of *Astragalus Membranaceus,* Huanqi, wherein the composition comprises at least one kidney-tonifying herb or an extract thereof and at least one herb or an extract thereof for respiratory disorders.

Another aspect of the present invention contemplates a method for the treatment or prophylaxis of an allergic or inflammatory reaction such as but not limited to a Type I hypersensitivity reaction (e.g. IgE-based allergic reaction) and in particular a respiratory disorder in a mammal, said method comprising administering an effective amount of the composition as hereinbefore described for a time and under conditions sufficient to treat or prevent said allergic or inflammatory reaction.

DETAILED DESCRIPTION OF THE PREFERRED EMBODIMENTS

Figure 1:
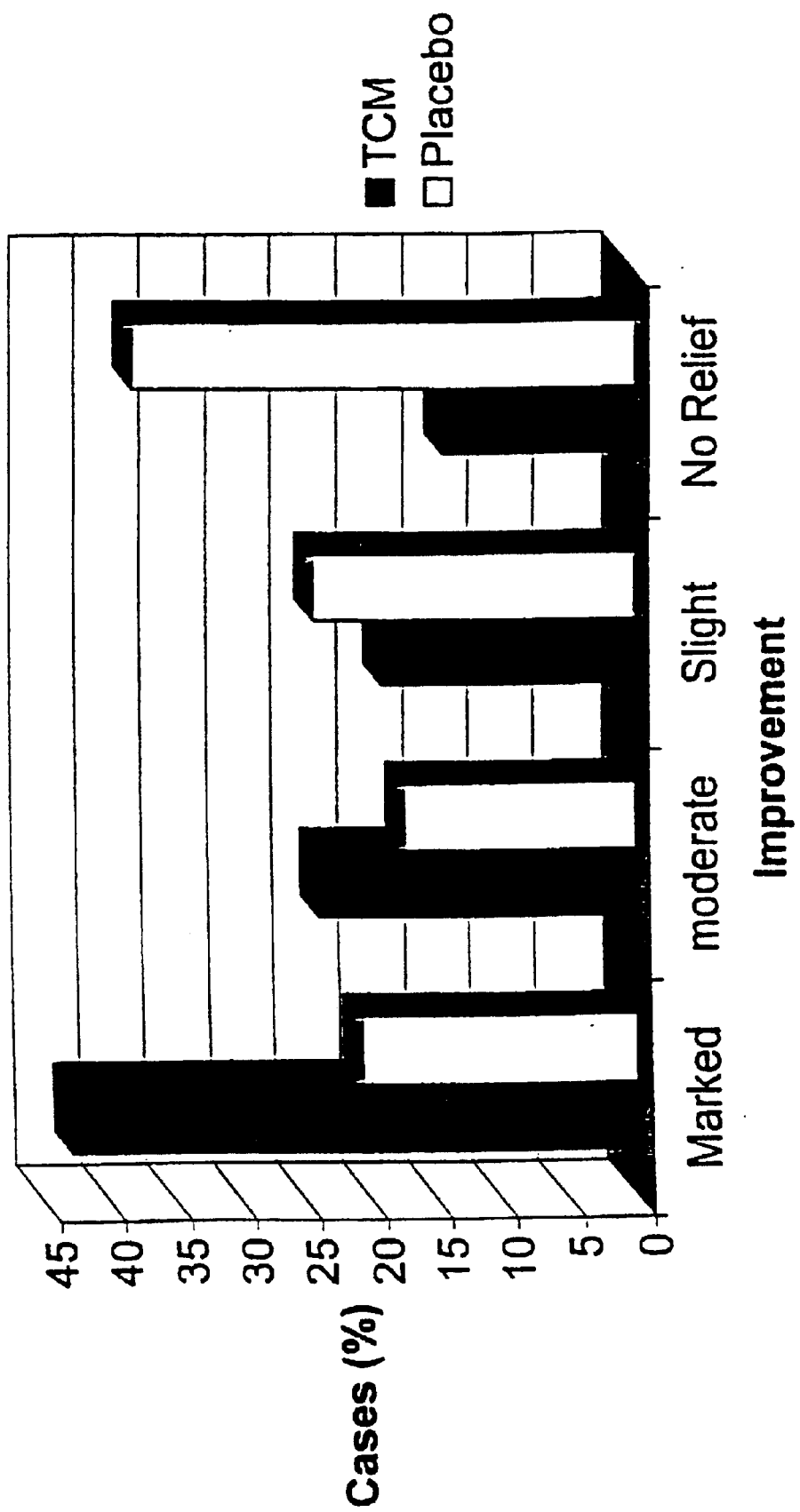
FIG. 1 is a graphical representation comparing the physician's assessment of patients having placebo (□) and herbal composition (Traditional Chinese Medicine [TCM]; ■). The improvement following treatment was rated as being marked, moderate, slight or no relief.

The present invention is predicated in part on the identification of a combination of herbs or an extract of herbs which is effective in the prophylaxis or treatment of allergic and inflammatory reactions in mammals.

In one embodiment, the allergic and inflammatory reaction is a Type I hypersensitivity reaction.

The term "Type I hypersensitivity reaction" is used in its broadest sense to include allergic rhinitis (hayfever), bronchial asthma, systemic anaphylaxis, wheal-and-flare and food allergy or other IgE-based allergic reactions. The preferred Type I hypersensitivity reaction in accordance with the present invention is an IgE-based respiratory disorder such as but not limited to allergic rhinitis (hay fever) and bronchial asthma.

Accordingly, one aspect of the present invention provides a composition comprising herbs or an extract of herbs or botanical or horticultural equivalents of herbs or chemical or functional equivalents of the herbal extract wherein said composition is effective in the prophylaxis or treatment of an allergic or inflammatory response.

Preferably, the allergic or inflammatory response is a Type I hypersensitivity reaction.

Preferably, the Type I hypersensitivity reaction results in allergic rhinitis or bronchial asthma.

The terms "treatment" and "prophylaxis" generally include the alleviation of symptoms or the prevention of symptoms or the inhibition of conditions resulting in the symptoms.

The composition of the present invention is conveniently shown to be effective in a placebo-controlled trial such as but not limited to a randomized, double-blind, placebo-controlled, parallel-grouped clinical trial.

Accordingly, another aspect of the present invention is directed to a composition comprising herbs or an extract of herbs or botanical or horticultural equivalents of herbs or chemical or functional equivalents of the herbal extract wherein said composition is effective in the prophylaxis or treatment of an allergic or inflammatory response as determined by a placebo-controlled trial.

The preferred herbs in the formulation of the present invention are those selected to:

(i) keep the airways open;
(ii) invigorate the spleen and digestive system;
(iii) reinforce the kidney and function of the urinary and reproductive system;
(iv) eliminate inflammation; and
(v) promote blood circulation and remove blood stasis.

Herbs are preferably selected on the basis of each of the above five principles. Herbs useful for each of these five principles are listed below:

(i) keep the airways open:

| | |
|---|---|
| Mahuang | The herb of *Ephedra Sinica* |
| Guizhi | The tender twig of *Cassia Cinnamomum* |
| Cangerzi | The fruit of *Xanthium Sibiricum* |
| Xinyi | The flower of *Magnolia Liliflora* |
| Bohe | The leaf of Field Mint |
| Xixin | The root of *Asarum Sieboldii* |
| Xingren | The kernel of Apricot |
| Chaihu | The root of *Bupleurum Chinense* |
| Yinxingye | The leaf of *Ginkgo Biloba* |
| Baizi | The root of *Angelcae Dahuricae* |
| Fangfeng | The root of *Ledebouriella Divaricata* | ii) invigorate the spleen and digestive system:

| | |
|---|---|
| Baizhu | The rhizome of *Atractylodes Macrocephala* |
| Shanyao | The rhizome of *Dioscorea Opposita* |
| Dangshen | The root of *Codonopsis Pilosula* |
| Dazao | The fruit of *Zizphus Jujuba* (Chinese date) |
| Gancao | The root of *Glycyrrhiza Uralensis* |
| Huangqi | The root of *Astragalus Membranaceus* |
| Huangjing | The rhizome of *Polygonatum Sibiricum* |

(iii) reinforce the kidney and function of urinary and reproductive system:

| | |
|---|---|
| Tusizi | The seed of *Cuscuta Chinensis* |
| Roucongrong | The stem of *Cistanche Salsa* |
| Fuzi | The root of *Aconiti Praceparata* |
| Yinyanghuo | The leaf of *Epimedium Sagittatum* |
| Buguzhi | The ripe fruit of *Psoralea Corylifolia* |
| Dihuang | The rhizome of *Rehmannia Glutinosa* |
| Xianmao | The rhizome of *Curculigo Orchioides* |

(iv) eliminate the inflammation:

| | |
|---|---|
| Huangqin | The root of *Scutellaria Baicalenis* |
| Wumei | The unripe fruit of *Prunus Mume* without seed |
| Wuweizi | The fruit of *Schisandra Chinensis* |

(v) promote the blood circulation and remove the blood stasis:

| | |
|---|---|
| Taoren | The kernel of *Prunus Persica* (peach) |
| Chuanxiong | The rhizome of *Ligusticum Wallichii* |
| Danpi | The root bark of *Moutan Radicis* |
| Chishao | The root of *Paeonia Lactiflora.* |

Accordingly, another aspect of the present invention comprises a composition comprising herbs or an extract of herbs or botanical or horticultural equivalents of herbs of chemical or functional equivalents of the herbal extract wherein said composition is effective in the prophylaxis or treatment of an allergic or inflammatory response and wherein said herbs in the composition are selected to:

(i) keep airways open;
(ii) invigorate the spleen and digestive system;
(iii) reinforce the kidney and function of the urinary and reproductive tract;
(iv) eliminate inflammation; and
(v) promote blood circulation and remove blood stasis.

More particularly, the present invention is directed to a composition comprising herbs or an extract of herbs of botanical or horticultural equivalents of herbs or chemical of functional equivalents of the herb extract wherein said composition is effective in the prophylaxis or treatment of an allergic or inflammatory response and wherein said herbs in the composition are selected from first, second, third, fourth and fifth groups of herbs wherein the first group comprises: Mahuang, Guizhi, Cangerzi, Xinyi, Bohe, Xixin, xingren, Chaihu, Yinxmgye, Baizi and Fangfeng; the second group comprises: Baizhu, Shanyao, Dangshen, Dazao, Gancao, Huanqi and Huangjing; the third group comprises: Tusizi, Roucongrong, Fuzi, Yinyanghuo, Buguzhi, Dihuang and Xianmao; the fourth group comprises: Huangqin, Wumei and Wuweizi; the fifth group comprises: Taoren, Chuanxiong, Danpi and Chishao.

Particularly preferred herbs in accordance with the present invention are selected from the list comprising: Dihuang; Huangqin; Huangjing; Yinxingye; Yinyanghuo; Buguzhi; Wuweizi; Wumei; Fangfeng;Baizi; and Huangqi or their botanical or horticultural equivalents.

Dihuang is the rhizome derived from *Rehmannia glutinosa* (Gaertn.) Libosch. (Scrophulariaceae) or *R. glutinosa* Libosch f. *hueichingensis* (Chao et Schih) Hsiao. The herb is also known as Shengdihuang, Shudihuang or Dihuangtan depending on the way it is processed. The main constituents of the herb are β-sitosterol and mannitol; other constituents include a small amount of stigmasterol and a trace amount of campesterol, and catalpol, rehmannin, and vitamin A. The rhizome of *R. glutinosa* f. *hueichingensis* also contains mannitol and catalpol.

Huangqin, also known as Kuqin, is the root of *Scutellaria baicalensis* Georgi (Labiatae). Its other sources are *Scutellaria viscidula* Bge. Huanghuahuangqin, *Scutellaria amoena* C. H. Wright Xi'nanhuangqin, *Scutellaria rehderiana* Diels, *Scutellaria Ikonnikovii* Juz., *Scuttelaria likiangensis* Diels, and *Scutellaria hypericifolia* Lévl.

The root contains 5 flavonoids: baicalein (scutellarein), baicalin (scutellarein-7-glucuronide), wogonin, wogonoside (wogonin-7-glucuronide) and neobaicalein. The root also contains β-sitosterol, benzoic acid and an enzyme of Huangqin.

Huangjing is the rhizome of *Polygonatum sibiricum* Redoute, *Polygonatum cyrtonema* Hua, *Polygonatum macropodium* Turez, *Polygonatum kingianum* Coll. et Hemsl., and *Polygonatum cirrhifolium* (Wall).

Huangjing contains mucilage. The rhizome of *P. cyrtonema* contains azetidine-2-carboxylic acid, aspartic acid, homoserine, digitalis glycoside, and anthraquinones.

Yinxingye is the leaf of *Ginkgo biloba* L. (Ginkgoceae) and contains flavonoids, ginkgetin, isoginkgetin, bilbobetin, quercetin, kaempferol, rhamnetin, isorhamnetin and kaempferol-3-rhamnoglucoside. It also contains bilobalide, rutin, 3'-O-Methylmyricetin-3-rhamnoglucoside and bitter principles ginkgolides A, B and C.

Yinyanghuo refers to the whole plant of *Epimedium sagittatum* (Sieb. et Zucc.) Maxim., *Epimedium brevicornum* Maxim. and *Epimedium macranthum* Morr. et Decne (Berberidaceae). The stem and leaf of *E. sagittatum* contain icariin, des-O-methylicariin, β-anhydroicaritin and magnoflorine. The underground part contains the flavone des-O-methyl-β-anhydroicaritin, icariins A, B, C, D and E, and lignan.

Buguzhi refers to the ripe fruit of *Psoralea corylifolia* L. (Leguminosae). Its other names are Heiguzi and Poguzhi. The ripe fruit of *P. corylifolia* contains flavonoids corylifolin (bavachin), corylifolinin (isobavachalcone), bacachromene and noebavachalcone, coumarins, psoralen, angelicin (isopsoralen), psoralidin, isopsoralidin and corylidin, and monoterpene phenols bakuchiol, and volatile oil, fixed oil, and resin.

Wuweizi, also known as Beiwuwiezi, is the fruit of *Schisandra chinensis* (Turcz.) Baill. (Schisandraceac). It is also derived from *Schisandra sphenanthera* Rehd. et Wils.

The fruit of *S. chinensis* contains schizandrin, deoxyschizandrin, γ-Tschizandrin, pseudo-γ-schizandrin and schizandrol. Seven pharmacologically active compounds have been isolated from an ethanol extract of the herb, five of which were identified as schizandrins C, B, and A, and schizandrols A and B. Schizandrol A is schizandrin, schizandrin B is γ-schizandrin, and schizandrin A is deoxyschizandrin. The herb contains approximately 3% of volatile oil from which α-chamigrene, β-chamigrene and chamigrenal were isolated. It also contains citral, β-sitosterol, citric acid and vitamins C and E.

Wumei is the unripe fruit of *Prunus mume* Sieb. et. Zucc (Rosaceae) and contains large amounts of citric acid, malic acid, succinic acid, tartaric acid and oleanolic acid. The seed contains amygdalin.

Fangfeng is the root derived from *Ledebouriella divaricata* (Turcz.) Hiroe (*Ledebouriella seseloids* (Hoffm.) Wolff.; *Siler divaricatum* Benth. et Hook. f.; *Saposhnikovia divaricata* (Turcz.) Schischk.; *Stenocoelium divaricatum* Turcz) (Umbelliferae). Its other names are Guanfangfeng and Chefangfeng. The herb contains volatile oil, mannitol, bitter glycosides, phenolic compound, polysaccharides and organic acids.

Baizi (*Radix Angelicae dahuricae*) is the dry root of *Angelica dehurica* (Fisch. ex Hoffm.) Benth. et Hook f. or *A. dahurica* var. *formosana* (Boiss) Shan et Yuan (Apiaceac) collected between summer and fall when the leaves have turned yellow.

The roots of *A. dahurica* and *A. dahurica* var. *formosana* are known to contain a number of coumarin and furocoumari derivatives.

Huangqi is the root of *Astragalus membranaceus* (Fisch.) Bge., or *A. membranaceus* Bge. var. *mongholicus* (Bge.) Hsiao (Leguminosae). The root of *A. membranaceus* contains 2'4'-dihydroxy-5,6dimethoxyisoflavone, kumatakenin, choline, betaine, polysaccharides, glucuronic acid and traces of folic acid.

The present invention extends to any or all of the above-mentioned herbs or botanical or horticultural equivalents thereof as well as chemical or functional equivalents of the extracts prepared from the herbs. The present invention is not necessarily limited, however, to the major constituents of the herbs since efficacious amounts of a combination of trace elements or constituents of the above-mentioned herbs may also be required. A botanical or horticultural equivalent of a herb is a plant which is physiologically, biochemically, immunologically, structurally or functionally similar to a herb or herbal extract or which exhibits therapeutically similar properties. For example, many Australian native plants have medicinal value which may be used to supplement or substitute for a herb.

In a preferred embodiment of the present invention, the composition comprises at least five of the above-mentioned herbs or extracts of at least five of the above-mentioned herbs or botanical or horticultural equivalents of the herbs or chemical or functional equivalents of the herbal extract.

Accordingly, another aspect of the present invention contemplates a composition comprising five or more herbs or extracts thereof or botanical or horticultural equivalents of the herbs or chemical or functional equivalents of the herbal extracts, said herbs selected from the list comprising at least one from five groups of herbs wherein the fist group comprises: Mahuang, Guizhi, Cangerzi, Xinyi, Bohe, Xixin, Xingren, Chaihu, Yinxingye, Baizi and Fangfeng; the second group comprises: Baizhu, Shanyao, Dangshen, Dazao, Gancao, Huangqi and Huangjing; the third group comprises: Tusizi, Roucongrong, Fuzi, Yinyanghuo, Buguzhi, Dihuang and Xianmao; the fourth group comprises: Huangqin, Wumei and Wuweizi; the fifth group comprises: Taoren, Chuanxiong, Danpi and Chishao.

Preferably, the composition comprises at least six, more preferably at least seven, even more preferably at least eight, still more preferably at least nine, even still more preferably at least ten, yet more preferably at least eleven herbs or extracts of eleven herbs or their botanical or horticultural equivalents or chemical or functional equivalents of the herbal extracts wherein the herbs are selected from Mahuang, Guizhi, Cangerzi, Xinyi, Bohe, Xixin, Xingren, Chaihu, Yinxingye, Baizi, Fangfeng, Baizhu, Shanyao, Dangshen, Dazao, Gancao, Huangqi, Huangjing, Tusizi, Roucongrong, Fuzi, Yinyanghuo, Buguzhi, Dihuang, Xianmao, Huangqin, Wumei, Wuweizi, Taoren, Chuanxiong, Danpi and Chishao.

One particularly useful composition for treating allergic or inflammatory conditions comprises an extract of the following herbs: Dihuang; Huangqin, Huangjing; Yinxingye; Yinyanghuo; Buguzhi; Wuweizi; Wumei; Fangfeng; Baizi, and Huangqi or botanical or horticultural equivalents of said herbs or chemical or functional equivalents of said herbal extracts.

Still another useful composition comprises five or more herbs or extracts of five or more herbs selected from the list comprising:

the rhizome of *Rehmannia Glutinosa Libosch,* Dihuang; the root of *Scutellaria Baicalensis Georgi,* Huangqin; the rhizome of *Polygonatum Sibiricum Redoute,* Huangjing; the leaf of *Ginkgo Biloba,* Yinxingye; the leaf of *Epimedium Sagittatum,* Yinyanghuo; the ripe fruit of *Psoralea Corylifolia,* Buguzhi; the fruit of *Schisandra Chinensis Baill,* Wuweizi; the unripe fruit of *Prunus Mume Sieb* without seed, Wumei; the root of *Ledebouriella Divaricata Hiroe,* Fangfeng; the root of *Angelcae Dahuricae,* Baizi; the root of *Astragalus Membranaceus,* Huangqi, wherein the composition comprises at least one kidney-tonifying herb or an extract thereof and at least one herb or an extract thereof for respiratory disorders.

In a most preferred embodiment, the composition comprises the following herbs or extracts thereof in approximate percentage amounts shown in parentheses:

| | |
|---|---|
| the rhizome of *Rehmannia Glutinosa Libosch,* Dihuang | (5–50% w/w) |
| the root of *Scutellaria Baicalensis Georgi,* Huangqin | (5–20% w/w) |
| the rhizome of *Polygonatum Sibiricum Redoute,* Huangjing | (5–20% w/w) |
| the leaf of *Ginkgo Biloba,* Yinxingye | (5–50% w/w) |
| the leaf of *Epimedium Sagittatum,* Yinyanghuo | (5–50% w/w) |
| the ripe fruit of *Psoralea Corylifolia,* Buguzhi | (5–20% w/w) |
| the fruit of *Schisandra Chinensis Baill,* Wuweizi | (5–40% w/w) |
| the unripe fruit of *Prunus Mume Sieb* without seed, Wumei | (2–15% w/w) |
| the root of *Ledebouriella Divaricata Hiroe,* Fangfeng | (5–20% w/w) |
| the root of *Angelcae Dahuricae,* Baizi | (5–20% w/w) |
| the root of *Astragalus Membranaceus,* Huangqi | (5–50% w/w) |

The compositions of the present invention may also comprise one or more pharmaceutically acceptable carriers and/or diluents. Such carriers and/or diluents include any and all solvents, water, dispersion media, coatings, antibacterial and antifungal agents, isotonic and absorption delaying agents and the like. Preferably, the diluent is water or a water or alcohol based extract of the herb.

The composition may be in the form of capsules, tablets, buccal tablets, troches, elixers, suspensions, syrups, wafers and the like. They may also be in a form which may be inhaled or given by nasal spray, aerosol droplets or vapour infusion.

One particularly important allergic and inflammatory condition to treat is allergic rhinitis. A standardized formulation for treating allergic rhinitis meets the following criteria:
(i) herbs are selected on the basis of the five groups outlined above;
(ii) the formulation is balanced; for example, the herbs with a warm nature are of equal strength as the herbs with a cold nature, so that the formulation is applicable to most patients;
(iii) an average dose of each herb is used. Generally, around 50–200 g of dry herbs comprised of about 5 to 20 herbs are considered to be the average daily dosage for a short-term treatment. For a long-term treatment, the average daily dosage would be reduced to between ½ and ⅕.

In a particularly preferred embodiment, the herbs are contained and subjected to conventional extraction techniques. Such techniques include water extraction, solvent extraction, alcohol extraction and/or acid or base extraction. The resulting extract is then preferably incorporated into a capsule.

Another aspect of the present invention contemplates a method for the treatment or prophylaxis of an allergic or inflammatory reaction such as but not limited to a Type I hypersensitivity reaction (e.g. IgE-based allergic reaction) and in particular a respiratory disorder in a mammal, said method comprising administering an effective amount of the composition as hereinbefore described for a time and under conditions sufficient to treat or prevent said allergic or inflammatory reaction.

Preferably, the disorder is allergic rhinitis or hayfever.

Mammals contemplated herein include humans, primates, laboratory test animals (eg. mice, rabbits, guinea pigs, hamsters), livestock animals (eg. cows, sheep, horses, pigs), companion animals (e.g. dogs, cats) or captive wild animals.

Preferably, the mammal is a human.

Preferably, the compositions are provided orally such as in capsule, where multiple capsules are consumed hourly, daily, weekly or monthly.

The invention is hereinafter described in relation to the specific treatment of allergic rhinitis. This is done, however, with the understanding that a similar treatment protocol is applicable to other allergic or inflammatory conditions.

A "symptom differentiation method" is employed to select the best combination of herbs. One such symptom differentiation method is as follows.

(i) Differentiation of Symptoms and Signs

These are Yin and Yang (all the opposing factors), Biao (superficial of the body) and Li (interior), Xu (asthenia or weakness) and Shi (sthenia or above normal), Han (cold) and Re (heat).

(ii) Differentiation of Functions and Relations of the Organs

To differentiate whether the symptoms are related to or affect the organ(s).

(iii) Differentiation of Qi (Vital Energy) and Xue (Blood or Essence of the Body)

Qi and Xue are not only a pair of material and its function, but also a general indicator of the health of the whole body, similar to the general principle of Yin and Yang.

The following is an example showing a diagnostic and treatment protocol for treating an allergy or inflammation.

1. A patient presents with an allergy or inflammatory disorder.
2. A symptom differentiation method is applied and a determination is made if there is a weakness and/or deficiency.
3. A determination of whether Yin deficiency or Yang deficiency exists. If Yang deficiency, symptoms have a cold nature and are accompanied by pale face, cold limbs, pale and enlarged tongue, weakness or diarrhea.
4. A determination is made if organs are involved. If lungs involved, check for asthma, cough, fever and colour of sputum. If there is asthma with cough and yellow sputum, then lung infection likely.
5. Conclusion: allergic rhinitis and asthma as main diagnosis.
6. TCM differentiation of symptoms: weakness of the lungs with evil heat (infection).
7. Prepare formulation based on selecting at least five herbs wherein at least one herb is selected from each of the following groups: the first groups comprises: Mahuang, Guizhi Cangerzi, xinyi, Bohe, Xixin, Xingren, Chaihu, Yinxingye, Baizi and Fangfeng; the second group comprises: Baizhu, Shanyao, Dangshen, Dazao, Gancao, Huangqi and Huangjing; the third group comprises: Tusizi, Roucongrong, Fuzi, Yinyanghuo, Buguzhi, Dihuang and Xianmao; the fourth group comprises: Huangqin, Wumei and Wuweizi; the fifth group comprises: Taoren, Chuanxiong, Danpi and Chishao.

The formulation of allergic rhinitis is balanced and is safe and suitable for most patients with allergic rhinitis including patients with high blood pressure, heart, kidney and liver diseases and pregnancy. The formulation for allergic rhinitis may be modified in accordance with the differentiation of symptoms and accompanied diseases to meet the nature and characteristics of the patient:

If Qi (vital energy) deficiency of the lungs:

Symptoms and signs: severe itching, sneezing and runny nose are the main symptoms, coldness, aversion to cold and pale face and tongue are minor symptoms.

Modification of the formulation: Add Dangshen (the root of *Codonopsis Pilosula*) or Ginseng and/or increase the dose of Huangqi (the root of *Astragalus Membranaceus*) to strengthen the general vital energy; select more kidney reinforcing herbs such as Tusizi (the seed of *Cuscuta Chinensis*), Roucongrong (the stem of *Cistanche Salsa*) to enhance the vital energy of kidney and lungs.

If Qi deficiency of the spleen:

Symptoms and signs: Severe blocked nose, often with headache, fatigue, thirst and poor appetite, cannot concentrate. The tongue is often pale and enlarged with tooth marks.

Modification of the formulation: Consider Baizhu (the rhizome of *Atractylodes Macrocephala*), Shanyao (the rhizome of *Dioscorea Opposita*) and/or Dangshen to reinforce the vital energy of the spleen. Chenpi (the dried orange peel) and Cangzhu (the rhizome of *Atractylodes Chinensis*) to improve the digestive function.

If Yang deficiency of the kidneys:

Symptoms and signs: Long history of the disease, generally feel weak and cold, with pale face, cold limbs, sore back and insomnia, pale tongue and weak pulse.

Modification of the formulation: Consider Tusi (the seed of *Cuscuta Chinensil*), Roucongrong (the stem of *Cistanche Salsa*), Xianmao (the rhizome of *Curculigo Orchioides*), Rougui (the bark of Chinese cassia tree) and Fuzi (the root of *Aconiti Pracparata*) to strengthen the reinforcement of the kidney Yang.

If Allergic rhinitis with asthma:

If asthma occurs in normally peak seasons, treat the asthma.

Suggest cease tonics with ascending characteristics, such as Dangshen (the root of *Codonopsis Pilosula*), Huangqi (the root of *Astragalus Membranaceus*) and reduce the tonics with warm nature (Fuzi—the root of *Aconiti Pracparata,* Rougui—the bark of Chinese cassia tree).

Give anti-asthmatic herbs: Mahuang (the herb of *Ephedra Sinica*), Gualou (the fruit of *Trichosanthes Kirilowii* or *Trichosanthes Uniflora*) and Gancao (the root and rhizome of *Glyeyrrhiza Uralensis*).

If within an interval of the seasonal asthma attack, reinforce the kidney (vital energy), same as the treatment of kidney weakness (deficiency of vital energy).

If with chest and/or sinus infection, consider antipyretic and anti-cough herbs, such as: Huzhang (the rhizome of *Polygoni Cuspidati*), Yuxingcao (the herb of *Houttuynia Cordata*), Zhuli (bamboo juice), Cangzhu (the rhizome of *Atractylodes Chinensis*), Qianhu (the root of *Peucedanum Decursivum*) and Ziwan (the root of *Aster Tataricus*).

If Allergic rhinitis with urticaria and/or eczema:

If with urticaria, add some herbs for relieving the skin from the endogenous factor of wind: Jinyinhua (the flower of *Lonicera Japonica*), Baixianpi (the root-bark of *Dictamni Radicis*), Chishao (the root of *Paeonia Lactiflora*) and Gegen (the root of kudzu vine).

If with eczema, consider the following herbs to dispel the pathological factor of dampness from the skin: Kushen (the root of *Sophora Flavescens*), Tufuling (the rhizome of *Smilacis Glabrae*), Cangzhu (the rhizome of *Atractylodes Chinensis*), and Yimi (the seed of *Cois Lachryma*).

If with irritable bowel syndrome, add Baishao (the root of *Paeonia Lactiflora*), Baizhu (the rhizome of *Atractylodes Macrocephala*), Dangshen (the root of *Codonopsis Pilosula*) and baked Ginger.

The present invention is further described by the following non-limited examples.

EXAMPLE 1

Preparation of Herbal Formulation

The herbal formulation comprises extracts from eleven herbs. The herbs employed and their percentage amounts are shown in Table 1.

TABLE 1

| HERB | % AMOUNT (w/w) |
|---|---|
| The rhizome of *Rehmannia Glutinosa Libosch*, DIHUANG | 10% |
| The root of *Scutellaria Baicalensis Georgi*, HUANGQIN | 10% |
| The rhizome of *Polygonatum Sibiricum Redoute*, HUANGJING | 8% |
| The leaf of *Ginkgo Biloba*, YINXINGYE | 10% |
| The leaf of *Epimedium Sagittatum*, YINYANGHUO | 10% |
| The ripe fruit of *Psoralea Corylifolia*, BUGUZHI | 10% |
| The fruit of *Schisandra Chenensis Baill*, WUWEIZI | 8% |
| The unripe fruit of *Prunus Mume Sieb* without seed, WUMEI | 4% |
| The root of *Ledebouriella Divaricara Hiroe*, FANGFENG | 10% |
| The root of *Angelcae Dahuricae*, BAIZI | 8 |
| The root of *Astragalus Membranaceus*, HUANGQI | 12% |

EXAMPLE 2

Extraction and Formulation

Herbal extraction techniques were performed according to standard protocols and were designed to maintain maximal levels of active components. Extracts of the eleven herbs listed in Table 1 were formulated into a Traditional Chinese Medicine (BIMIN) capsule.

EXAMPLE 3

Principles for Preparation of Formulation from Allergic Rhinitis

Herbs are required to be selected from five groups or principles of herbs. These five principles are:

(1) Keep the airways open;
(2) Invigorate the spleen and function of digestive system;
(3) Reinforce the kidney and function of urinary and reproductive system;
(4) Eliminate the inflammation;
(5) Promote the blood circulation and remove the blood stasis.

EXAMPLE 4

Formulation for the Treatment of Allergic Diseases

A formulation for the treatment of allergic diseases is prepared according to selecting herbs from the principles outlined in Example 4. At least one herb is selected from each of the following five principles:

(i) keep the airways open:

| Mahuang | The herb of *Ephedra Sinica* |
|---|---|
| Guizhi | The tender twig of *Cassia Cinnamomum* |
| Cangerzi | The fruit of *Xanthium Sibiricum* |
| Xinyi | The flower of *Magnolia Liliflora* |
| Bohe | The leaf of Field Mint |
| Xixin | The root of *Asarum Sieboldii* |
| Xingren | The kernel of Apricot |
| Chaihu | The root of *Bupleurum Chinense* |
| Yinxingye | The leaf of *Ginkgo Biloba* |
| Baizi | The root of *Angelcae Dahuricae* |
| Fangfeng | The root of *Ledebouriella Divaricata* |

(ii) invigorate the spleen and function of the digestive system:

| Baizhu | The rhizome of *Atractylodes Macrocephala* |
|---|---|
| Shanyao | The rhizome of *Dioscorea Opposita* |
| Dangshen | The root of *Codonopsis Pilosula* |
| Dazao | The fruit of *Zizphus Jujuba* (Chinese date) |
| Gancao | The root of *Glycyrrhiza Uralensis* |
| Huangqi | The root of *Astragalus Membranaceus* |
| Huangjing | The rhizome of *Polygonatum Sibiricum* |

(iii) reinforce the kidney and function of urinary and reproductive system:

| Tusizi | The seed of *Cuscuta Chinensis* |
|---|---|
| Roucongrong | The stem of *Cisianche Salsa* |
| Fuzi | The root of *Aconiti Praceparata* |
| Yinyanghuo | The leaf of *Epimedium Sagittatum* |
| Buguzhi | The ripe fruit of *Psoralea Corylifolia* |
| Dihuang | The rhizome of *Rehmannia Glutinosa* |
| Xianmao | The rhizome of *Curculigo Orchioides* |

(iv) eliminate the inflammation:

| Huangqin | The root of *Scutellaria Baicalenis* |
|---|---|
| Wumei | The unripe fruit of *Prunus Mume* without seed |
| Wuweizi | The fruit of *Schisandra Chinensis* |

(v) promote the blood circulation and remove the blood statis:

| Taoren | The kernel of *Prunus Persica* (peach) |
|---|---|
| Chuanxiong | The rhizome of *Ligusticum Wallichii* |
| Danpi | The root bark of *Moutan Radicis* |
| Chishao | The root of *Paeonia Lactiflora*. |

EXAMPLE 5

Trial

The herbal composition of the present invention was tested in a randomized, double-blind, placebo-controlled, parallel-grouped clinical trial using patients diagnosed as having the symptoms of allergic rhinitis. A total of 101 patients with perennial allergic rhinitis were initially screening by clinical, haematological and immunological examination and 58 subjects were selected. During the 12 week trial, 8 participants decided to discontinue treatment resulting in 50 patients finishing the trial. The trial pharmacist randomized and dispensed capsules of either placebo or herbal composition ("TCM" for "Traditional Chinese Medicine"). Of the 50 patients, 29 received a placebo and 21 received herbs.

No adverse side effects were observed during the trial in the herbal treatment group.

Four different assessments were used for evaluating the trial outcomes:

Physician's overall assessment.
Visual analogue scores.
Quality of life questionnaires.
Daily symptom assessment scores.

Statistical Analysis

The physician's overall assessment showed significant improvement in the herbal (TCM) group compared with the placebo group (P=0.036; 2-Tailed; FIG. 1). The total effective rate was 85.7% in the TCM group and 62.7% in the placebo group. Marked relief rate was 42.9% in the TCM group and 20.7% in the placebo group. No relief rate was 14.3% in TCM group and 37.9% in placebo group.

Compared with the placebo group, the visual analogue score showed that TCM patients exhibited significant improvement in the treatment group as assessed by all five symptoms of allergic rhinitis (FIG. 2):

Sneezing (P=0.001) [2-tail significance]
Runny nose (P=0.000)
Itchy nose (P=0.000)
Blocked nose (P=0.011)
Itchy eyes (P=0.013)

Figure 2:
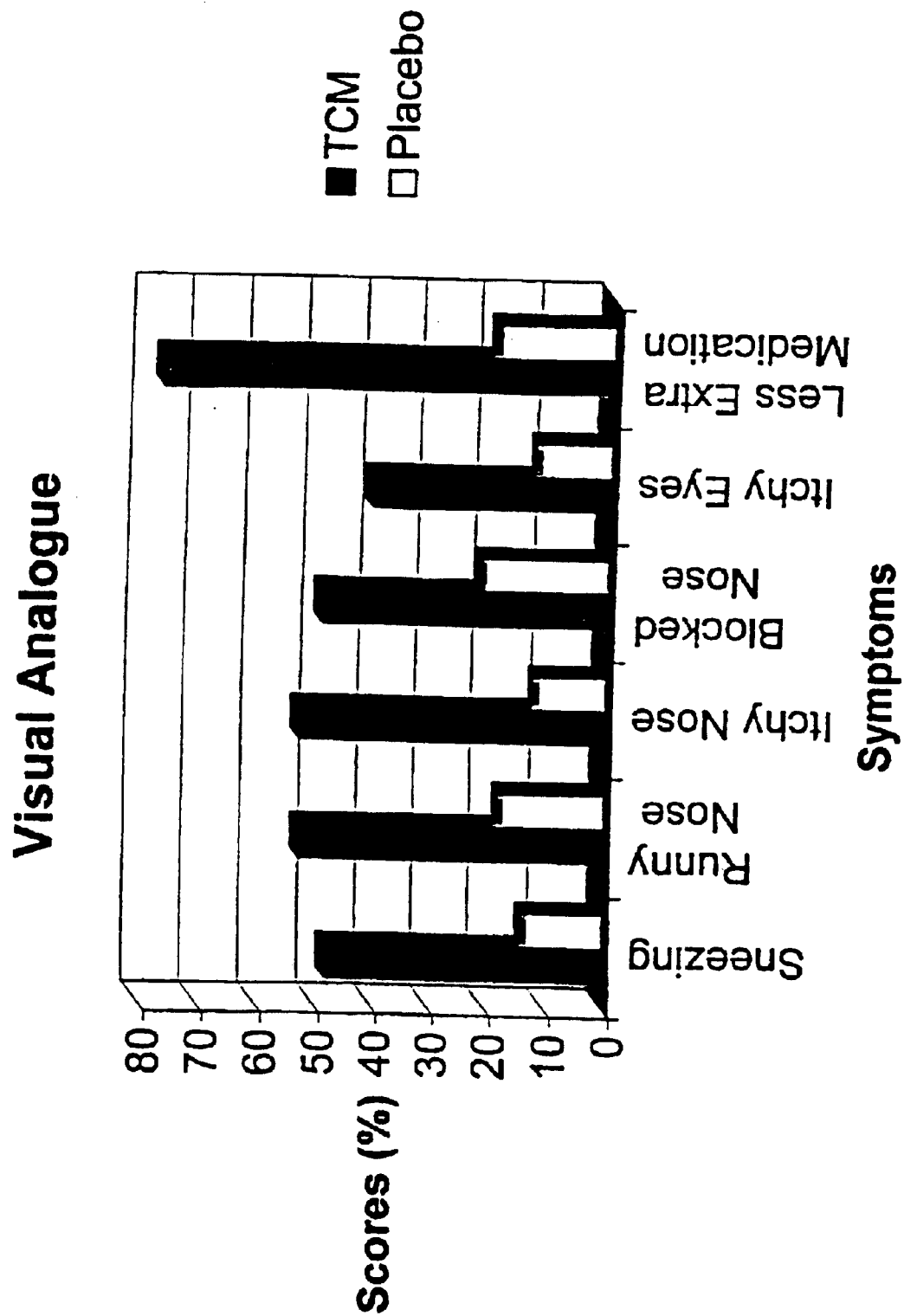
FIG. 2 is a graphical representation showing visual analogue assessment of herbal (TCM) patients (■) exhibiting significant improvement of the five major symptoms of allergic rhinitis, i.e. sneezing, runny nose, itchy nose, blocked nose and itchy eyes, compared to placebo patients (□).

Extra medication for relieving the symptoms of allergic rhinitis was also reduced significantly in the TCM group (P=0.000) [FIG. 2].

Figure 3:
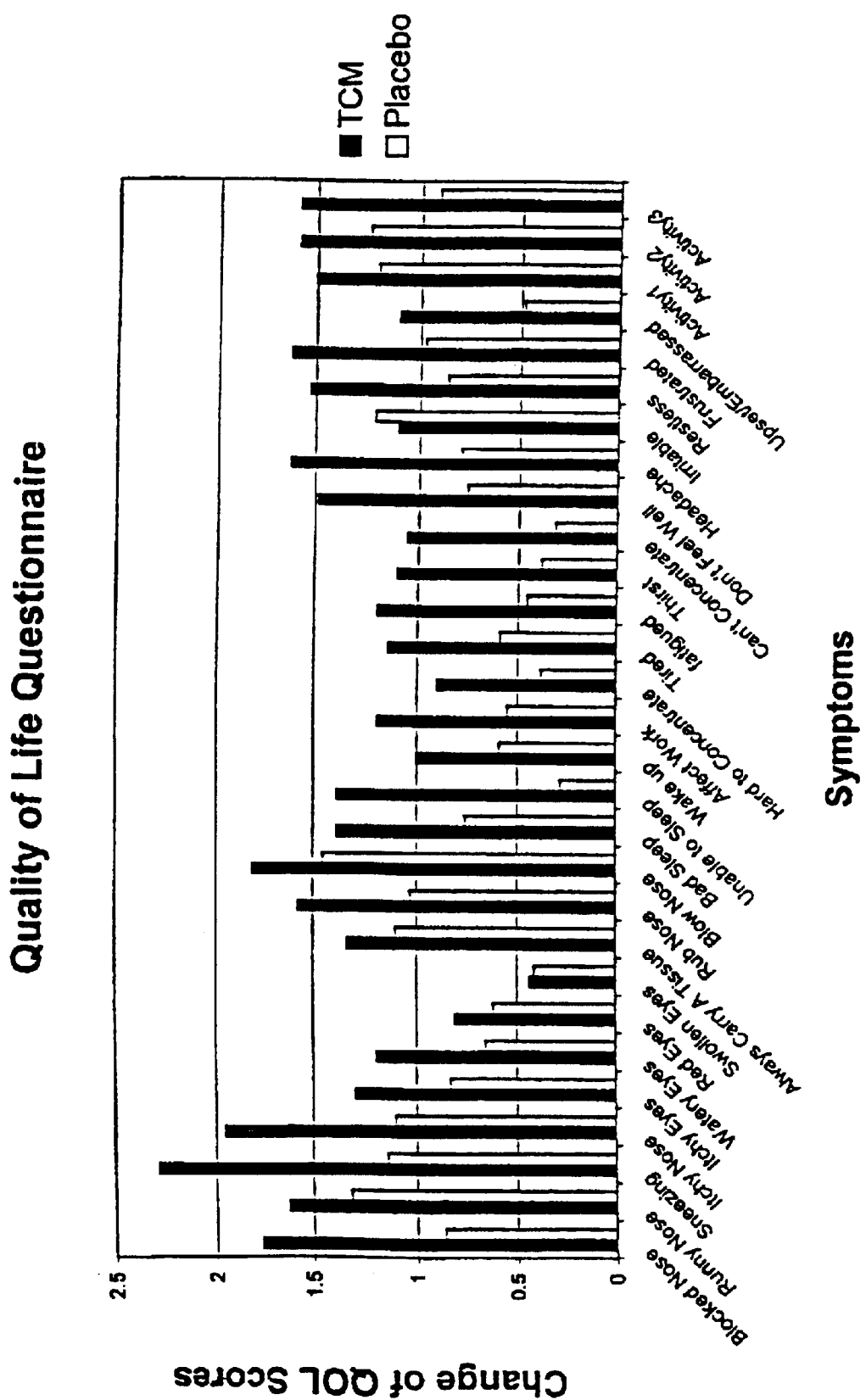
FIG. 3, is a graphical representation of the results of a quality of life questionnaire compiled by the patients of the clinical trial on various symptoms of allergic rhinitis. ■, TCM group; □, placebo group.

The quality of life scores assessed by the patients themselves were better in the TCM group compared with the placebo group (FIG. 3) with improvement in some of the symptoms reaching statistical significance:

Global improvement (P=0.048) [2-tail significance]
Sneezing (P=0.008)
Itchy nose (P=0.047)
Unable to go to sleep (P=0.014).

Figure 4:
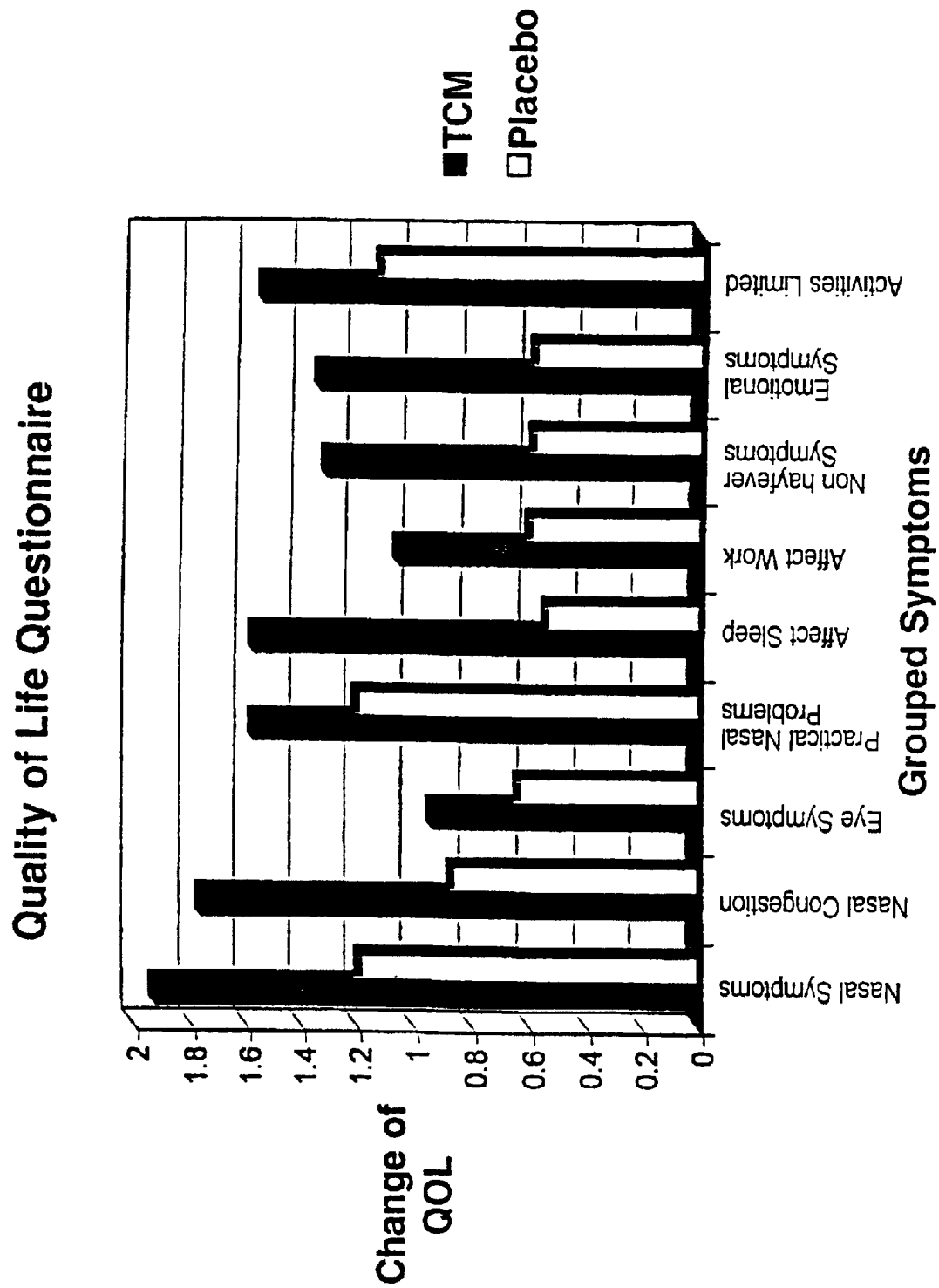
FIG. 4 is a graphical representation of the results of a quality of life questionnaire with the symptoms being grouped. ■, TCM group; □, placebo group.
Figure 5A:
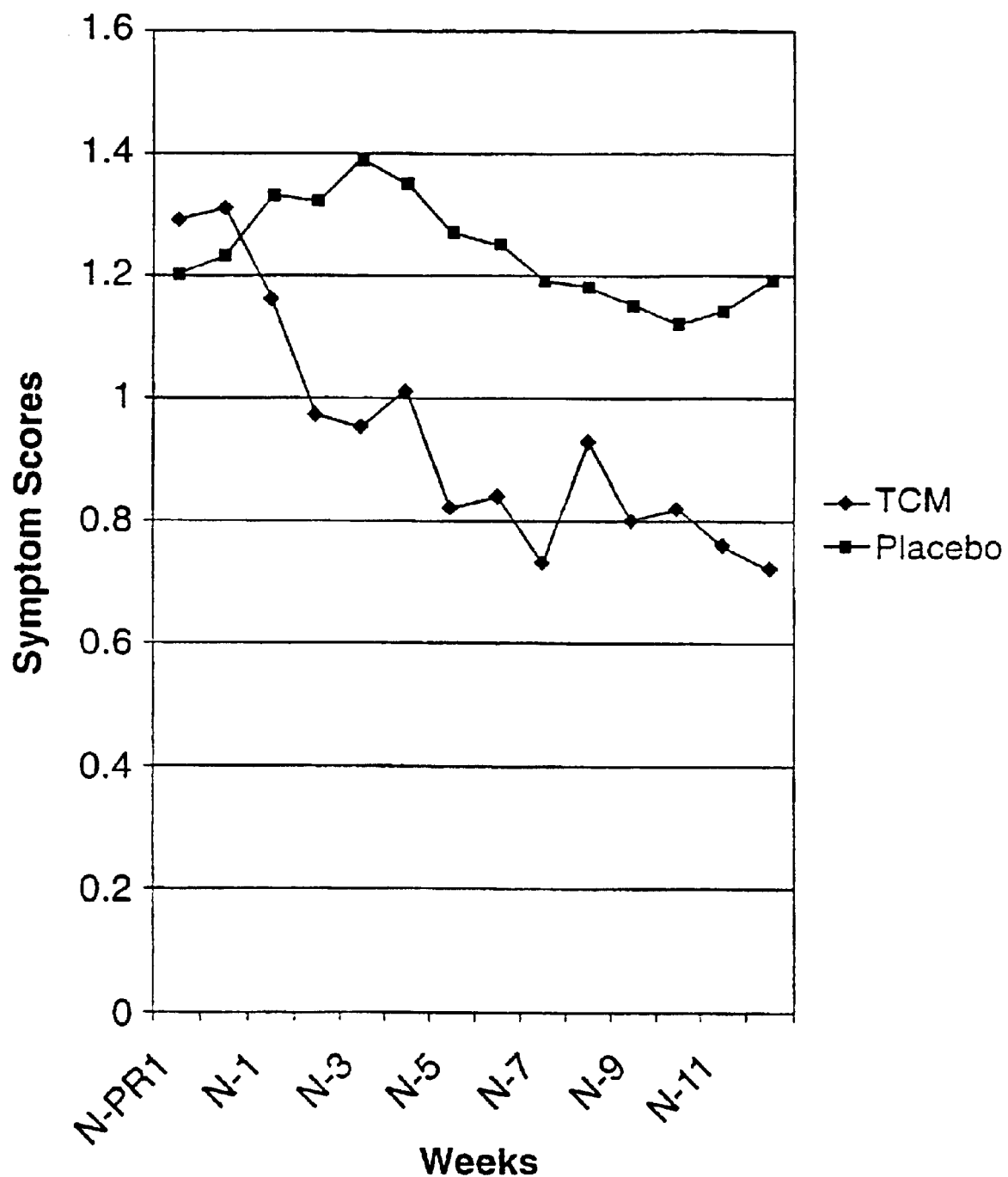
FIGS. 5a to 5e are graphical representations of symptom diary scores as determined by patients having TCM (-♦-) or placebo (-■-). a, itchy nose; b, sneezing; c, rhinorrhea; d, itchy eyes; and e, nasal congestion.
Figure 5B:
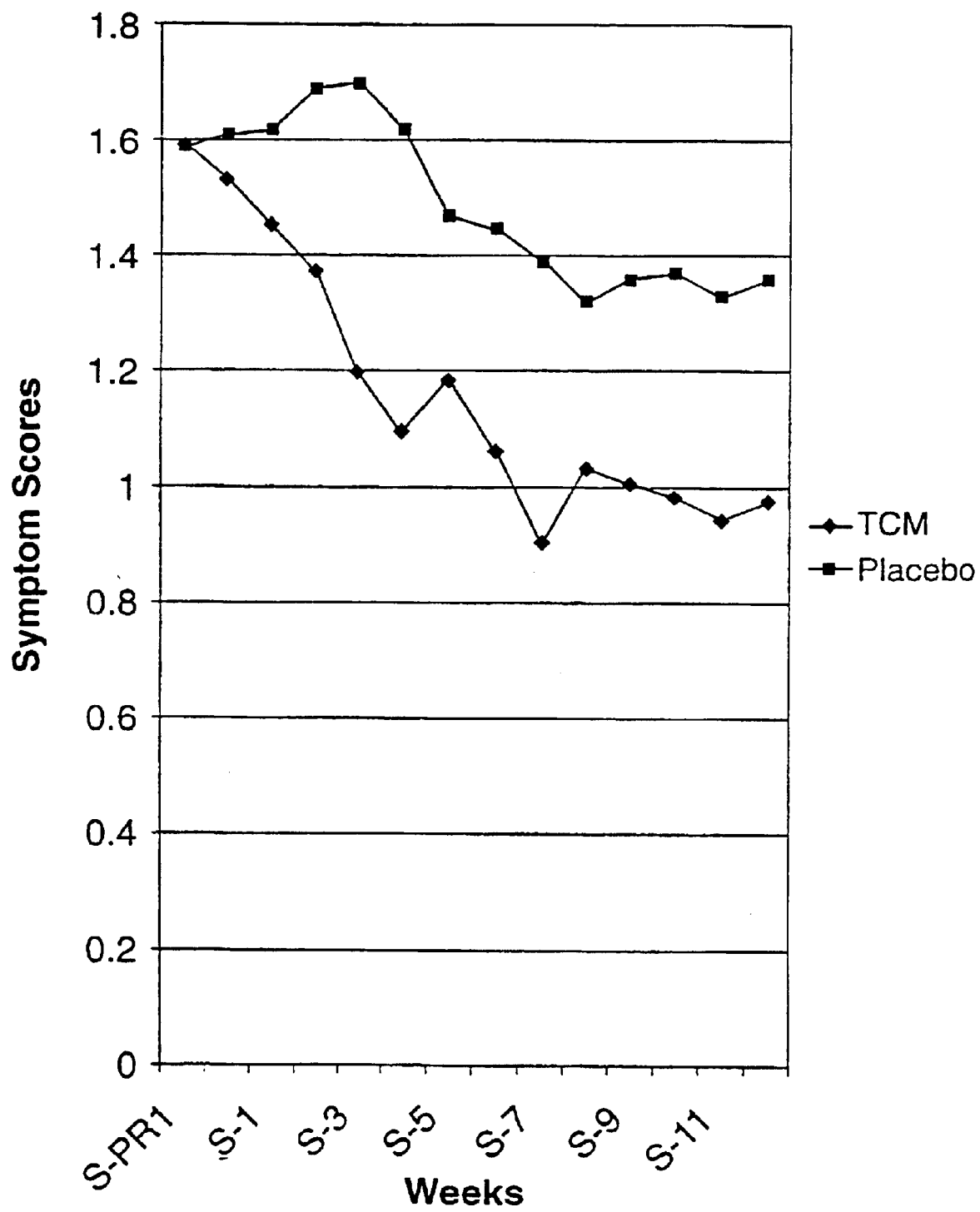
Figure 5C:
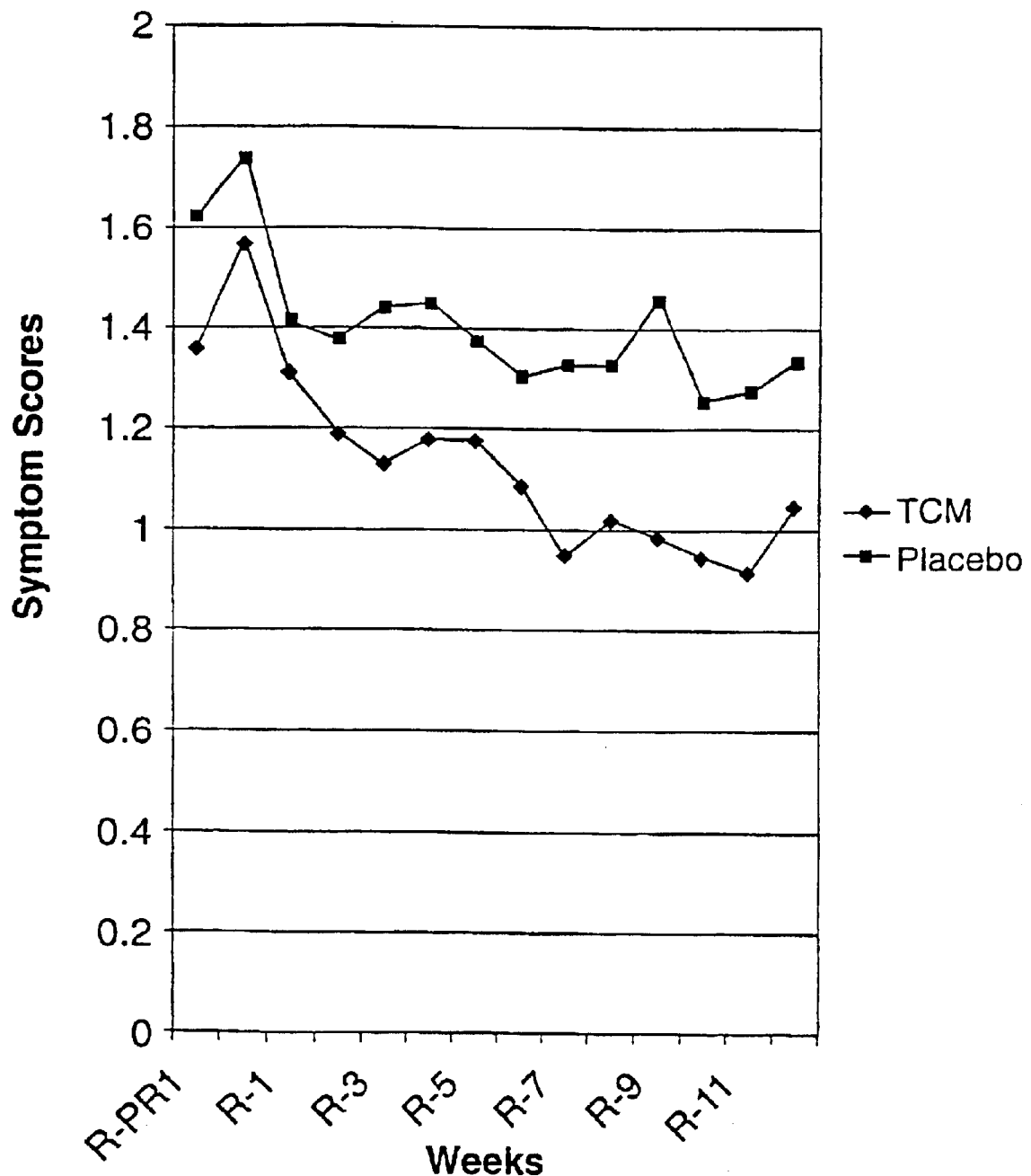
Figure 5D:
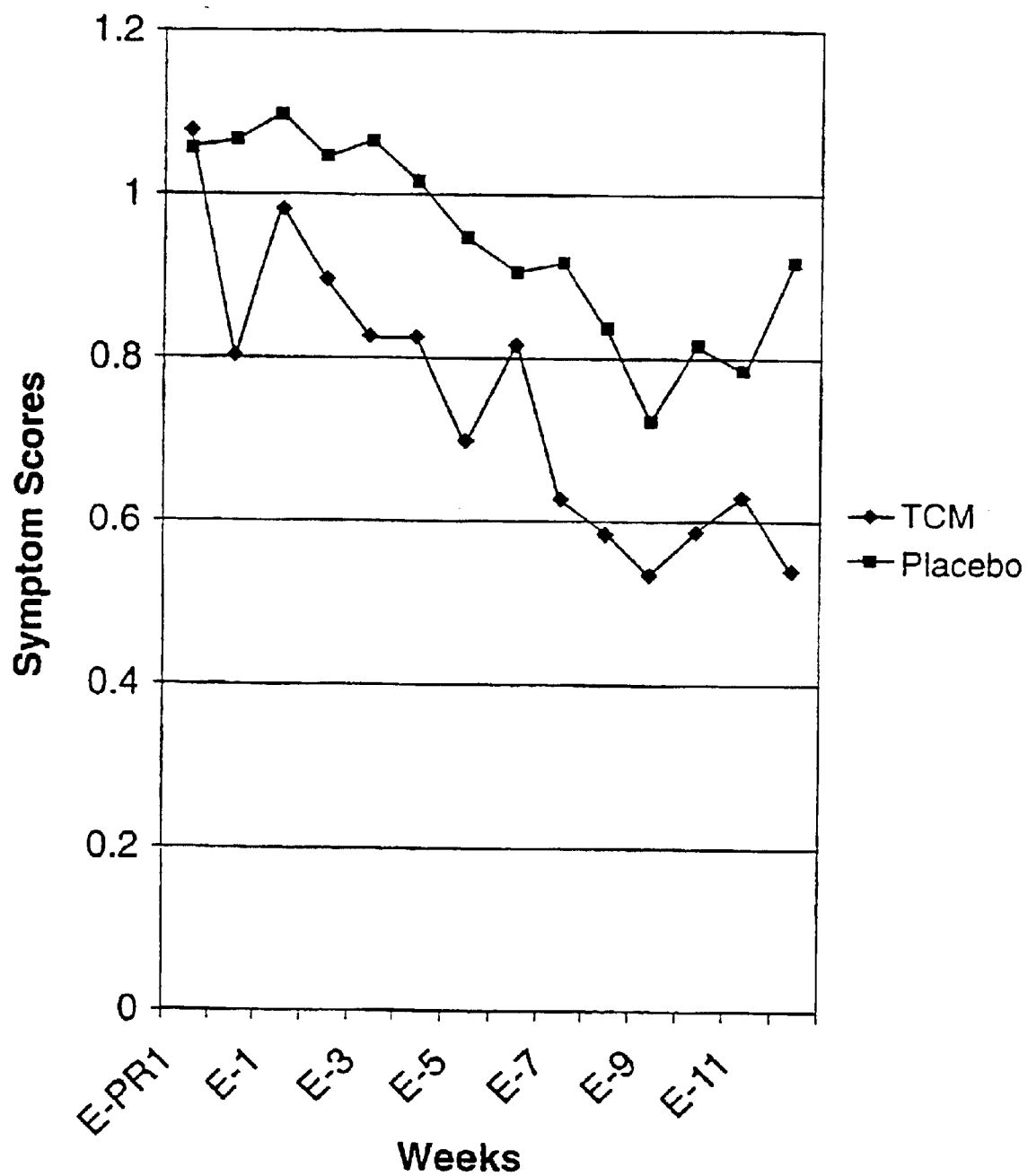
Figure 5E:
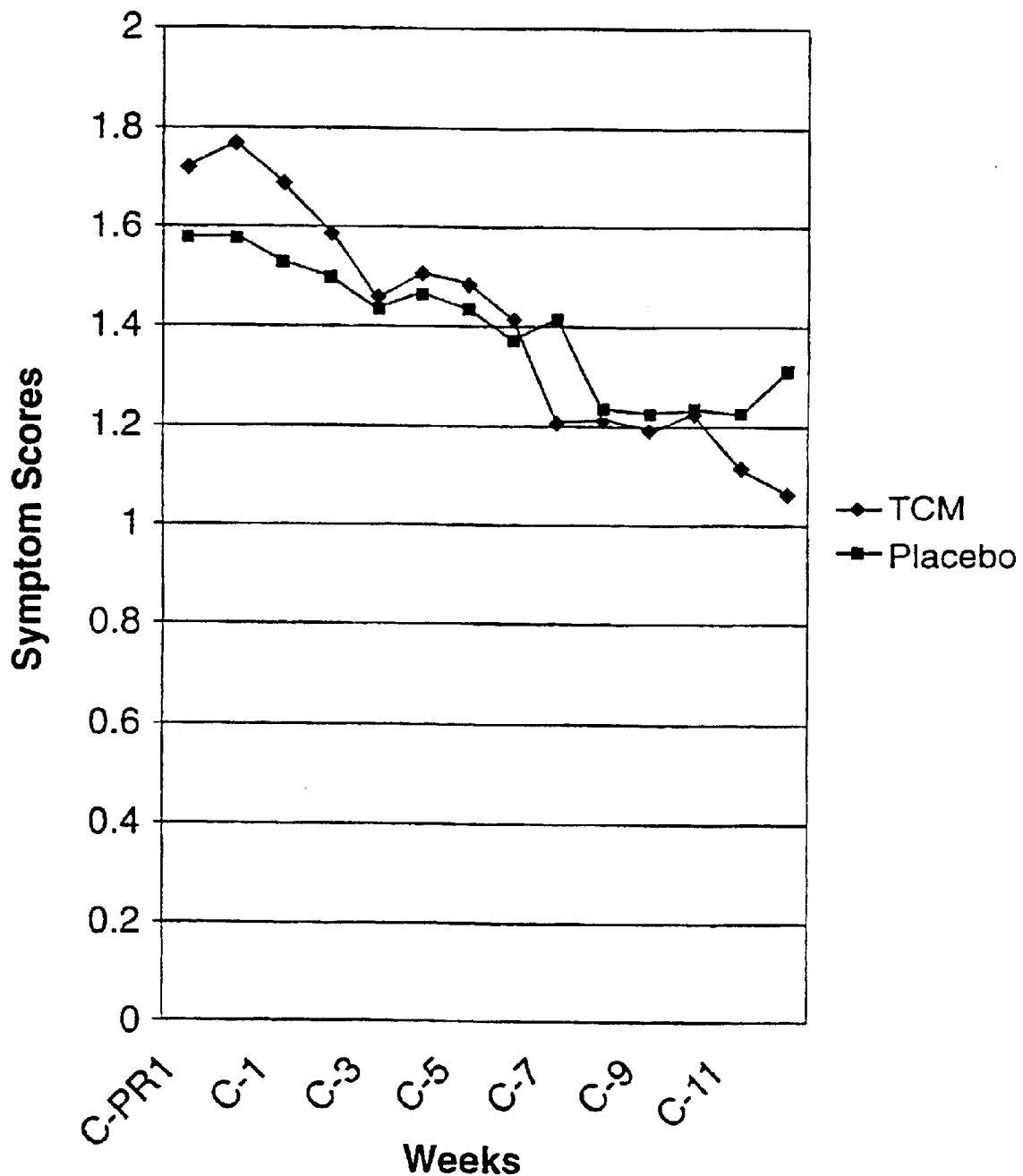
Figure 6A:
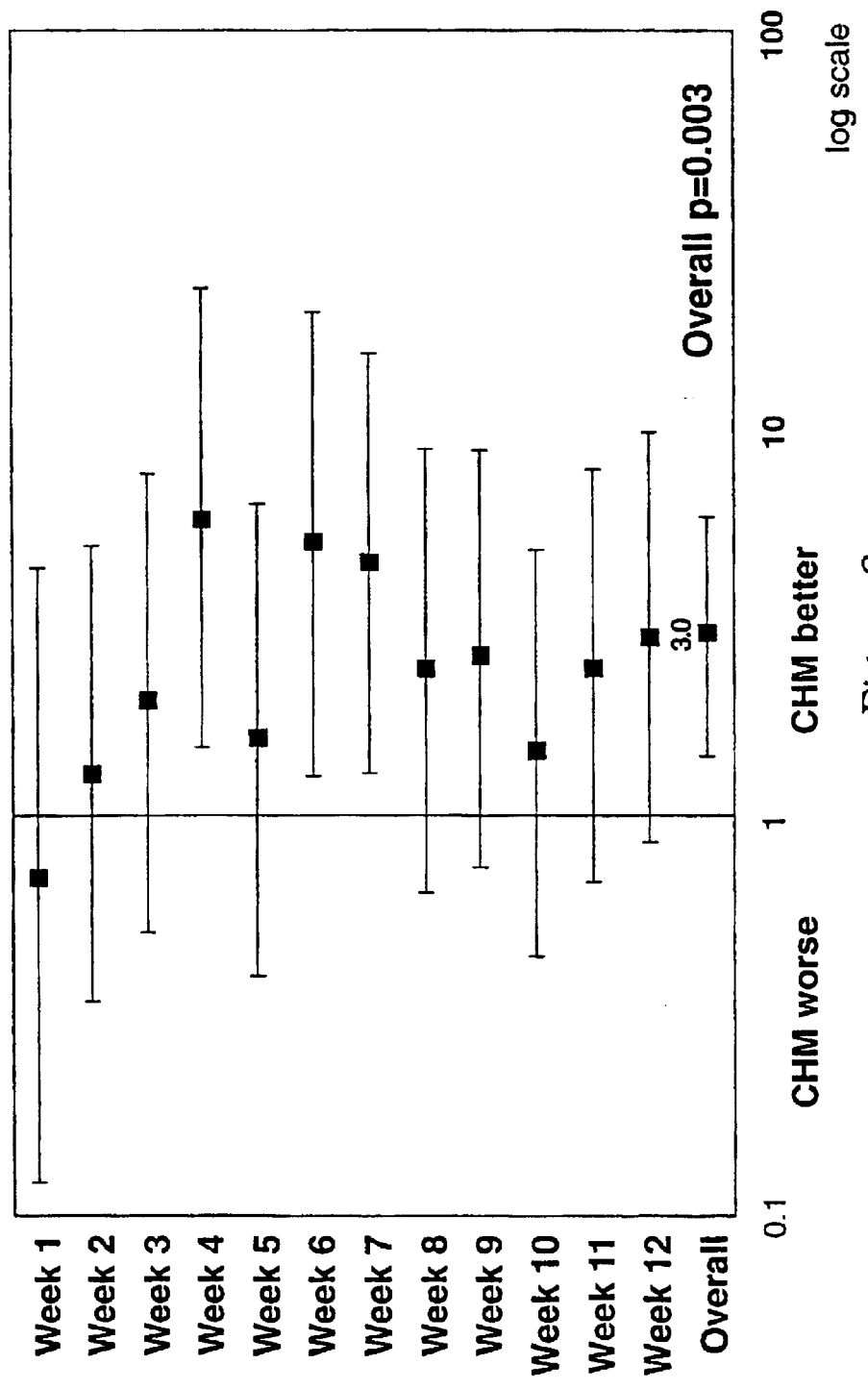
FIG. 6A is a graphic representation of Chinese herbal medicine versus placebo for treatment of hay fever odds ratio's (95% confidence limits): sneezing.
Figure 6B:
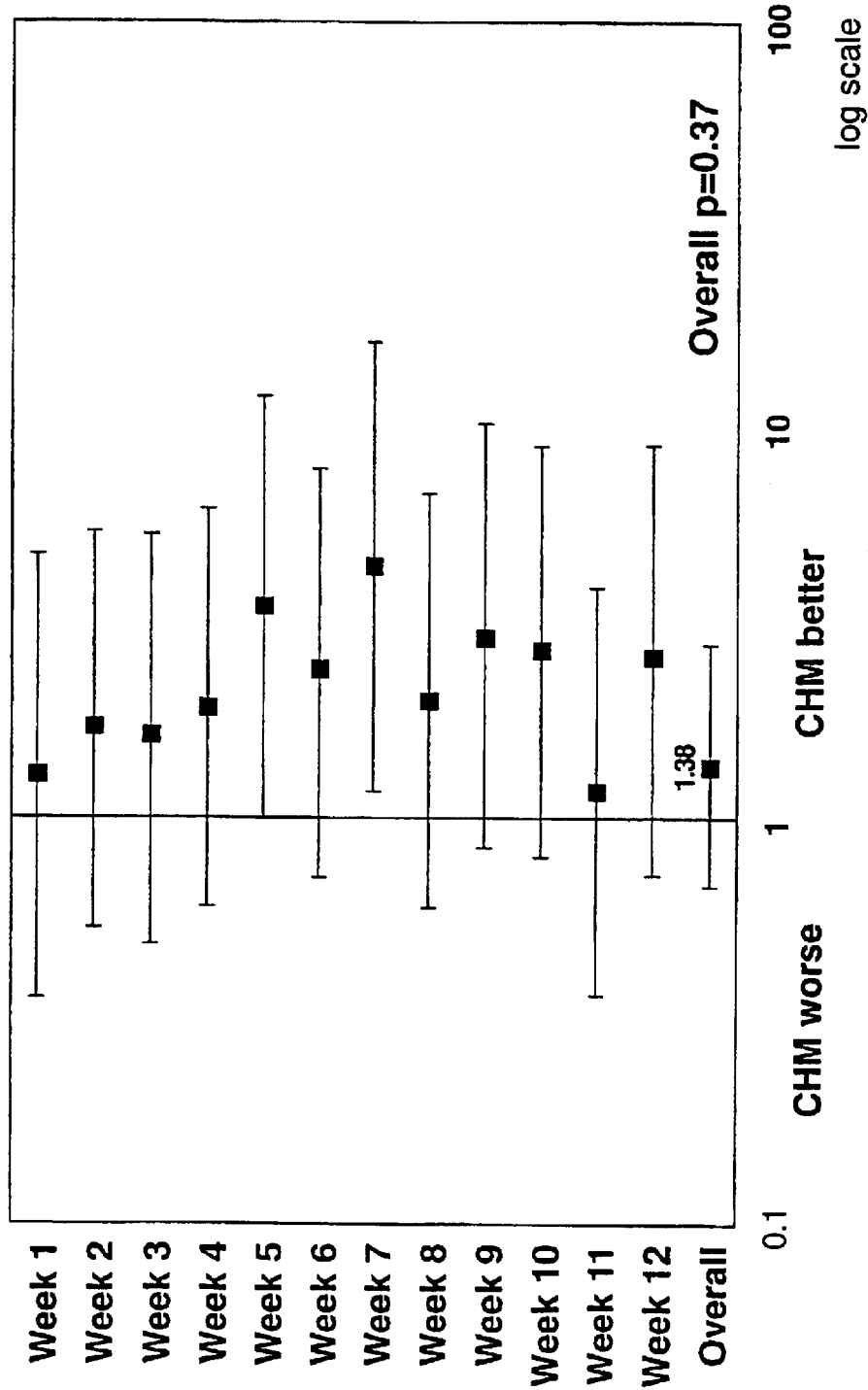
FIG. 6B is a graphical representation of Chinese herbal medicine versus placebo for treatment of hay fever odds ratio's (95% confidence limits): itchy nose.
Figure 6C:
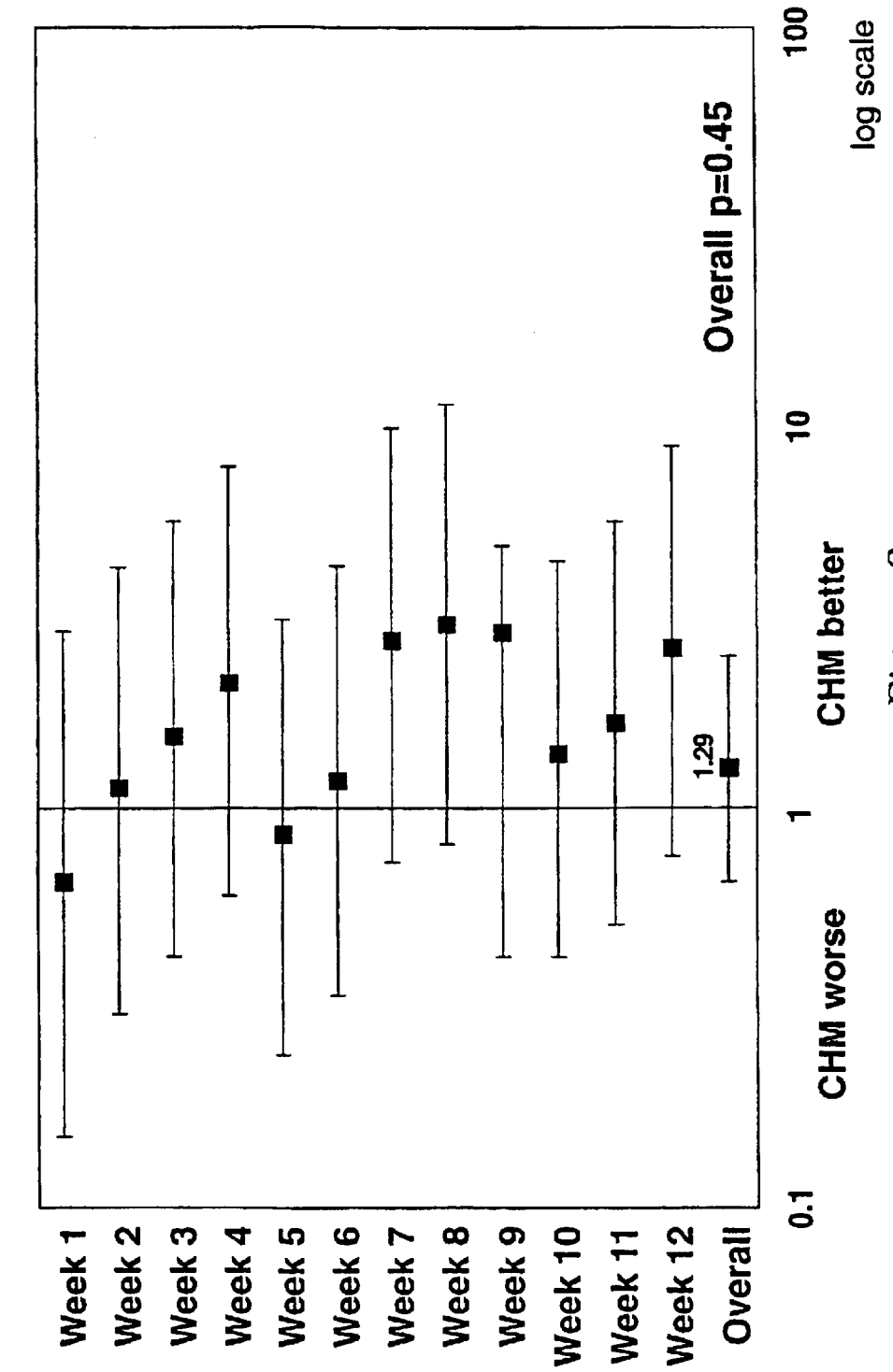
FIG. 6C is a graphical representation of Chinese herbal medicine versus placebo for treatment of hay fever odds ratio's (95% confidence limits): rhinorrhea.
Figure 6D:
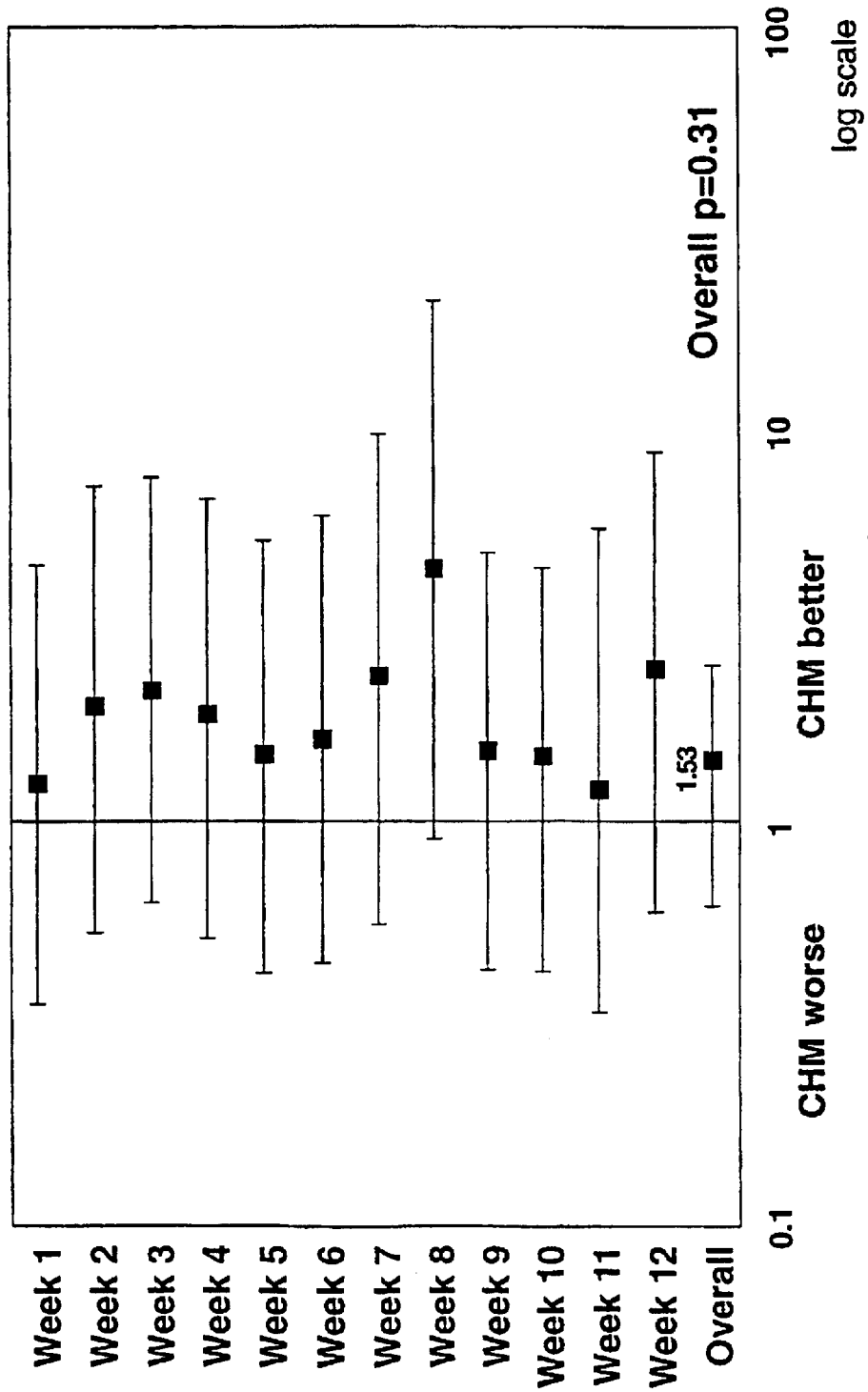
FIG. 6D is a graphical representation of Chinese herbal medicine versus placebo for treatment of hay fever odd ratio's (95% confidence limits): itchy, watery, red eyes.
Figure 6E:
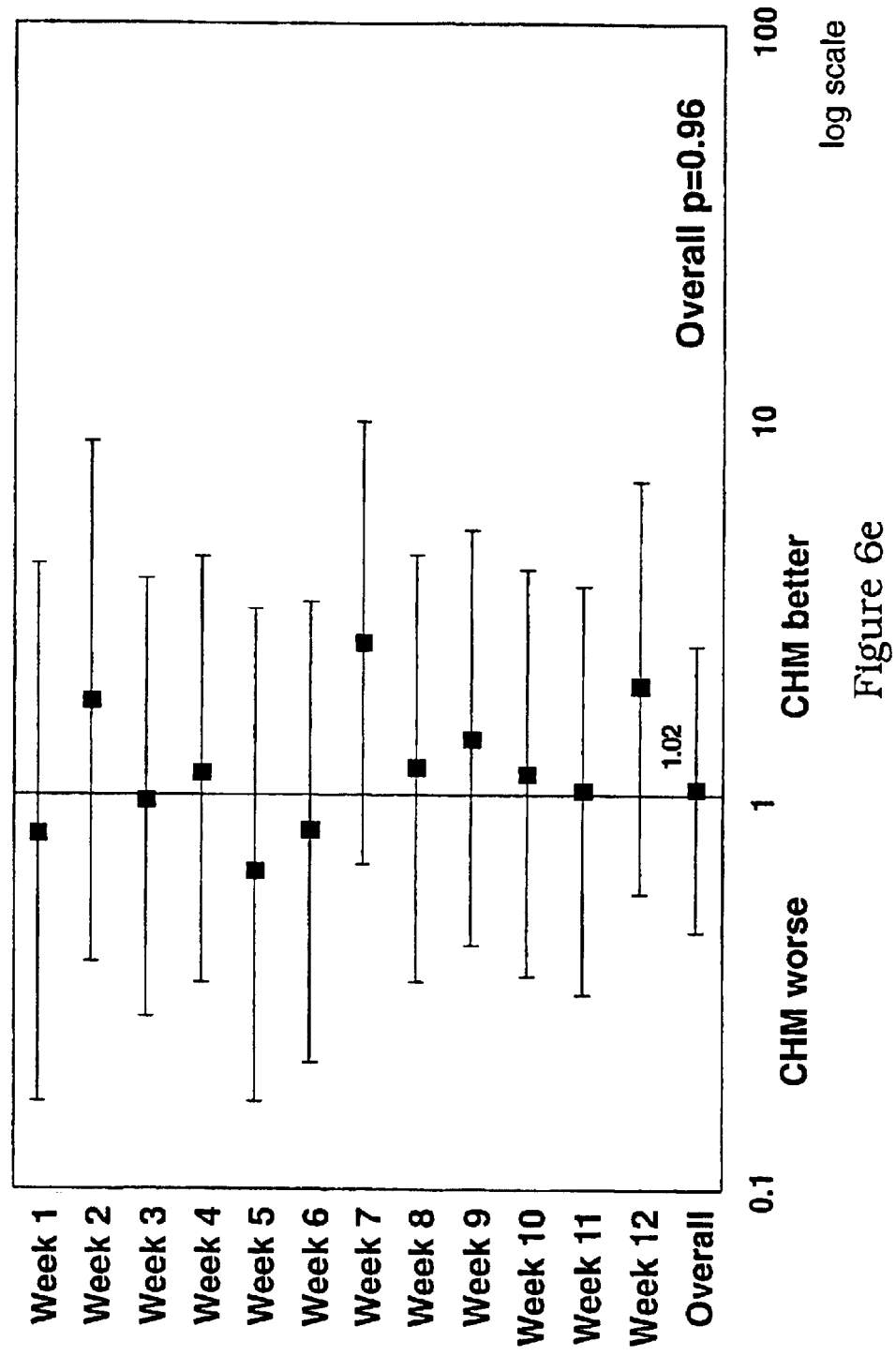
FIG. 6E is a graphical representation of Chinese herbal medicine versus placebo for treatment of hay fever odds ratio's (95% confidence limits): nasal congestion.

FIG. 4 shows the results of the quality of life questionnaire in terms of grouped symptoms.

Symptom diary scores assessed daily by patients showed a clear difference, and in particular showed that sneezing was significantly improved (see also Example 6) between TCM and Placebo groups (FIGS. 5a to 5e).

The trial showed a statistically significant improvement in treating allergic rhinitis or preventing development of allergic rhinitis.

EXAMPLE 6

Analysis of Trial of Chinese Herbal Medicine Versus Placebo for the Treatment of Hay Fever Methodology The following are points that describe the methodology used for analyzing five different daily symptom scores (sneezing, rhinorrhea, itchy watery red eyes, itchy nose and nasal congestion) measured on the 58 patients randomized to the study. Scores were taken for two weeks prior to treatment plus 12 weeks during the treatment phase.

1. The maximum pre-treatment symptom score was found (baseline) and dichotomized to:
    0,1=0 (mild or no symptoms)
    2–4=1 (moderate to very severe symptoms).
2. The maximum treatment phase symptom score for each week was found and dichotomized as described above.
3. Longitudinal logistic regression (Wei-Johnson method) adjusting for baseline was used to model the treatment phase symptom scores at each of the 12 post-treatment weeks plus overall.
4. All observations with missing values were deleted from the analysis.
5. Forest plots for each of the five different symptoms were presented using odds ratio's (+95% confidence limits) to describe the treatment effect at each of the 12 weekly time-points plus overall. A p-value was also given for the overall estimate.
6. An analysis using generalized estimating equations was used to check the results for each of the five different symptoms.

Interpretation

The results are shown in FIGS. 6A–6E.

The odds ratios is interpreted as follows:

Itchy, watery, red eyes: overall odds ratio 1.53

This means that the patients receiving placebo are 53% more likely to have moderate to very severe symptoms compared to patients receiving CHM.

Sneezing: overall odds ratio 3.0

This means that the patients receiving placebo are three times (300%) more likely to have moderate to very severe symptoms compared to patients receiving CHM.

The pots can be interpreted as follows:

For Rhinorrhea (overall odds ratio 1.29, p=0.45), Itchy Eyes (overall odds ratio 1.53, p=0.31) and itchy nose (overall odds ratio 1.38, p=0.37), there is a consistent trend over time in favour of CHM, however, this trends fails to reach statistical significance when scores at all the time-points are combined.

For sneezing (odds ratio 3.0, p=0.003), there is a consistent trend over time in favour of CHM and this trend is highly significant when scores at all the time-points are combined. Individual effects at weeks 4, 6 and 7 are also statistically significant.

For nasal congestion (odds ration 1.02, p=0.96), there is no evidence of an improved outcome for CHM over placebo.

EXAMPLE 7

Serum Total IgE Test

Patient serum was collected before and after the treatment during the 12-week clinical trial. Serum total IgE was tested using Pharmacia Unicap kit. Serum samples were coded and blinded to the test operator. Paired t test was used for statistics. The TCM group showed a significant decrease of serum total IgE after a three month herbal treatment (P=0.006) while the placebo group showed no significant changes (P=0.9287) (see Table 2).

TABLE 2

Effect of herbal treatment on serum IgE of PAR patients

| | Serum IgE (ku/L) (Mean * SD) | | |
|---|---|---|---|
| Group | Before treatment | After treatment | P |
| TCM | 412.6 ± 347.2 | 361.0 ± 296.6 | 0.006 |
| Placebo | 317.0 ± 314.7 | 309.9 ± 289.7 | 0.929 |

EXAMPLE 8

Dose Response Study

The dose the inventors used in the first clinical trial was actually double the traditional dose for long-term use. In order to test whether the half dose would be still working, the inventors carried out a dose response study in a randomized, double blind, parallel-grouped clinical trial. Twenty-two patients who had placebo in the last trial were recruited for this study. During 12 weeks trial, two patients decided to give up the study, twenty patients finished the trial. Patients were randomized into two groups: one group with full dose (same dose as last trial) and another with half dose (strength). Both groups had five capsules, twice a day. The trial pharmacists randomized the participants and dispensed the trial capsules.

(1) Physician's Overall Assessment

The total effective rates and marked+moderate effective rates in the two dose groups are very similar to that of the last clinical trial (85.7% and 66.7%, respectively). The effective rates in the half dose group are slightly higher than that in the full dose group.

TABLE 3

Physician's overall assessment

| Group | n | Total effective rate (%) (marked + moderate + slight) | Marked + moderate (%) |
|---|---|---|---|
| full dose | 10 | 80.0 | 60.0 |
| half dose | 10 | 90.0 | 90.0 |

(2) Visual Analogue Study

There is a clear trend in favour of the efficacy in both dose groups. There is no significant difference between dose groups. The improvement in the half dose group is still relatively higher than that in the full dose group.

TABLE 4

Improvement of visual analogue scores (%)

| Group | n | Total | Sneezing | Rhinorrhea | Itching nose | Itching eyes | Blocked nose | Extra medication |
|---|---|---|---|---|---|---|---|---|
| full dose | 10 | 34.9 | 33.2 | 34.0 | 37.0 | 45.1 | 23.9 | 36.2 |
| half dose | 10 | 40.3 | 48.0 | 25.0 | 46.4 | 54.1 | 40.4 | 27.8 |

(3) Quality of Life (QOL) Assessment

The QOF scores (pre-treatment minus post-treatment) have showed a consistent trend of improvement is both groups. The total scores in the full dose group are relatively higher than the half dose group but not significant.

TABLE 5

Improvement of QOL assessment (pre-post)

| Group | n | Total | Nasal symp | Nasal conj | Eye symp | Practical nasal problems |
|---|---|---|---|---|---|---|
| full dose | 10 | 0.66 ± 1.64 | 0.73 ± 2.10 | 0.80 ± 1.14 | 0.08 ± 2.02 | 0.87 ± 1.48 |
| half dose | 10 | 0.39 ± 1.65 | 0.56 ± 1.70 | 0.40 ± 1.42 | 0.55 ± 1.41 | 0.17 ± 1.84 |

| Group | Affect sleep | Affect work | Non-hayfever symp | Functional symp | Activity limited |
|---|---|---|---|---|---|
| full dose | 0.27 ± 1.48 | 0.95 ± 2.09 | 0.80 ± 1.50 | 0.35 ± 1.41 | 1.47 ± 1.22 |
| half dose | 0.70 ± 1.24 | 0.60 ± 1.67 | 0.48 ± 1.62 | 0.05 ± 1.75 | 0.00 ± 1.72 |

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

What is claimed is:

1. A composition comprising the following herbs:

the rhizome of *Rehmannia Glutinosa Libosch,* DiHuang; the root of *Scutellaria Baicalensis Georgi,* Huangqin; the rhizome of *Polygonatum Sibiricum Redout,* Huangjing; the leaf of *Ginkgo biloba,* Yinxingye, the leaf of *Epimedium Sagittatum,* Yinyanghuo, the ripe fruit of *Psoralea Corylifolia,* Buguzhi; the fruit of *Schisandra Chinesis Baill,* Wuweizi; the unripe fruit of *Prunus Mume Sieb* without seed, Wumei; the root of *Ledebouriella Divaricata Hiroe,* Fangfeng; the root of *Angelcae Dahuricae,* Baizi; and the root of *Astragalus Membranaceus,* Huangq.

2. A method for treating an allergic reaction, said method comprising administering an effective amount of the composition according to claim 1 for a time and under conditions sufficient to treat said allergic reaction.

3. A method for prophylaxis of an allergic reaction, said method comprising administering an effective amount of the composition according to claim 1 for a time and under conditions sufficient to provide prophylaxis of said allergic reaction.

4. A method for treating an inflammatory reaction, said method comprising administering an effective amount of the composition according to claim 1 for a time and under conditions sufficient to treat said inflammatory reaction.

5. A method for prophylaxis of an inflammatory reaction, said method comprising administering an effective amount of the composition according to claim 1 for a time and under conditions sufficient to provide prophylaxis of said inflammatory reaction.

* * * * *